United States Patent
Skovlund

(10) Patent No.: US 9,326,943 B1
(45) Date of Patent: May 3, 2016

(54) BIODEGRADABLE PROSTHESIS

(76) Inventor: Sandra M. Skovlund, Minneapolis, MN (US)

( * ) Notice: Subject to any disclaimer, the term of this patent is extended or adjusted under 35 U.S.C. 154(b) by 293 days.

(21) Appl. No.: 12/820,864

(22) Filed: Jun. 22, 2010

Related U.S. Application Data

(60) Provisional application No. 61/219,447, filed on Jun. 23, 2009.

(51) Int. Cl.
| | | |
|---|---|---|
| A61F 2/48 | (2006.01) | |
| A61F 2/64 | (2006.01) | |
| A61F 2/66 | (2006.01) | |
| A61F 2/68 | (2006.01) | |
| H02K 1/14 | (2006.01) | |
| H02K 5/14 | (2006.01) | |
| H02K 23/40 | (2006.01) | |
| G04C 13/11 | (2006.01) | |
| H02K 37/00 | (2006.01) | |
| H02K 1/22 | (2006.01) | |
| H02K 7/06 | (2006.01) | |
| H02K 7/10 | (2006.01) | |
| A61K 9/16 | (2006.01) | |
| F16H 3/06 | (2006.01) | |
| F16H 27/02 | (2006.01) | |
| F16H 29/02 | (2006.01) | |
| F16H 29/20 | (2006.01) | |
| F16K 31/02 | (2006.01) | |

(Continued)

(52) U.S. Cl.
CPC ......... *A61K 9/1658* (2013.01); *A61F 2002/183* (2013.01); *A61F 2210/0004* (2013.01); *A61F 2210/0061* (2013.01); *A61F 2230/0006* (2013.01); *A61F 2230/0069* (2013.01); *A61F 2250/0003* (2013.01); *A61F 2250/0039* (2013.01); *A61K 9/10* (2013.01)

(58) Field of Classification Search
CPC ........................................................ A61F 2/18
USPC ............................................................ 623/10
See application file for complete search history.

(56) References Cited

U.S. PATENT DOCUMENTS

| | | |
|---|---|---|
| 3,710,399 A | 1/1973 | Hurst |
| 4,094,303 A * | 6/1978 | Johnston ........................ 128/868 |

(Continued)

FOREIGN PATENT DOCUMENTS

WO   WO 2008/036368   3/2008

OTHER PUBLICATIONS

Raney, Rance W., "Myringoplasty and Tympanoplasty"; Baylor College of Medicinge Bobby R. Alford Department of Otolaryngology-Head and Neck Surgery, Feb. 16, 1995. Accessed at www.bcm.edu/oto/grand/21695.html.

(Continued)

*Primary Examiner* — Jacqueline Woznicki
(74) *Attorney, Agent, or Firm* — Fredrikson & Byron P.A.

(57) ABSTRACT

A body compatible and resorbable prosthesis has a tubular body incorporating denatured gelatin sponge material, either as a unitary gelatin sponge or as fragmented or powdered sponge material dispersed throughout a structurally self supporting medium. One version of the prosthesis uses the fragmented or powdered form of the gelatin sponge and is substantially homogeneous. An alternative prosthesis employs an inner tubular layer of gelatin film. The gelatin film layer is surrounded by an outer tubular layer, formed either of the gelatin sponge or the fragmented medium incorporating the gelatin sponge dispersion.

18 Claims, 3 Drawing Sheets

(51) Int. Cl.
  *A61F 2/18* (2006.01)
  *A61K 9/10* (2006.01)

(56) References Cited

U.S. PATENT DOCUMENTS

| | | | |
|---|---|---|---|
| 4,468,218 A | 8/1984 | Armstrong | |
| 4,601,723 A | 7/1986 | McGrew | |
| 4,650,488 A | 3/1987 | Bays et al. | |
| 5,053,040 A | 10/1991 | Goldsmith, III | |
| 5,061,280 A | 10/1991 | Prescott | |
| 5,137,523 A * | 8/1992 | Peerless et al. | 604/264 |
| 5,693,065 A | 12/1997 | Rains, III | |
| 5,893,828 A | 4/1999 | Uram | |
| 6,379,323 B1 | 4/2002 | Patterson | |
| 6,458,386 B1 | 10/2002 | Schacht et al. | |
| 6,632,423 B2 | 10/2003 | Jafari et al. | |
| 6,703,041 B2 | 3/2004 | Burns et al. | |
| 7,097,661 B2 | 8/2006 | Perry | |
| 7,163,557 B2 | 1/2007 | D'Eredita | |
| 7,244,272 B2 * | 7/2007 | Dubson et al. | 623/1.44 |
| 8,603,982 B2 * | 12/2013 | Ooya et al. | 514/17.2 |
| 2001/0003788 A1 | 6/2001 | Ball et al. | |
| 2002/0169142 A1 | 11/2002 | Jafari | |
| 2003/0018291 A1 | 1/2003 | Hill et al. | |
| 2003/0086899 A1 | 5/2003 | Jafari | |
| 2003/0187381 A1 | 10/2003 | Greenawalt et al. | |
| 2004/0175383 A1 | 9/2004 | Barr et al. | |
| 2007/0082052 A1 | 4/2007 | Bonassar et al. | |
| 2008/0031465 A1 | 2/2008 | Ball | |
| 2008/0260801 A1 * | 10/2008 | Ahlers et al. | 424/426 |
| 2009/0317448 A1 | 12/2009 | Bonassar et al. | |

OTHER PUBLICATIONS

Schraff, Scott A. "Contemporary Indications for Ventilation Tube Placement"; Current Opinion in Otolaryngology & Head and Neck Surgery, 2008, 16: 406-411.

Hekkenberg, Robert J. et al., Gelfoam/Gelfilm Patching Folliwing the Removal of Ventilation Tubes; The Journal of Otolaryngology, vol. 24. No. 6, 1995; pp. 362-363.

Puterman, Marc et al., "Gelfoam Plug Tympanoplasty Concomitant with Removal of Retained Ventilation Tubes"; International Journal of Pediatric Otorhinolaryngology (2005) 69, 57-60.

Hoffman, Karen K., et al., "Inner Ear Perfusion: Indicaitons and Applications"; Current Opinion in Otolaryngology & Head and Neck Surgery 2003, 11:334-339.

D'Eredita, Riccardo et al., "A New Absorbable Pressure-Equalizing Tube", Otolaryngology—Head and Neck Surgery; Jul. 2002, pp. 67-72.

Roberts, Meredith C., "New in Situ Crosslinking Chemistries for Hydrogelation", A Dissertation Submitted to the Faculty of the University of Utah, May 2008.

Wisenthal, Alain A., et al., "New Method for Packing the External Auditory Canal, Middle Ear Space, and Mastoid Cavities After Otolic Surgery"; The Journal of Otolaryngology, vol. 28m No. 5, 1999, pp. 260-265.

Sckolnick, Joshua S. et al., "Pediatric Myringoplasty: Factors that Affect Success—A Retrospective Study"; The Laryngoscope 118, Apr. 2008, pp. 723-729.

D'Eredita, Riccardo et al., "Tympanic Membrane Healing Process and Biocompatibility of an Innovative Absorbable Ventilation Tube"; Otology & Neurotology, 2005, 27: 65-70.

Weber, David E., "Tissue-Engineered Calcium Alginate Patches in the Repair fo Chronic Chinchilla Tympanic Membrane Perforations"; The Laryngoscope 116; May 2006, pp. 700-704.

* cited by examiner

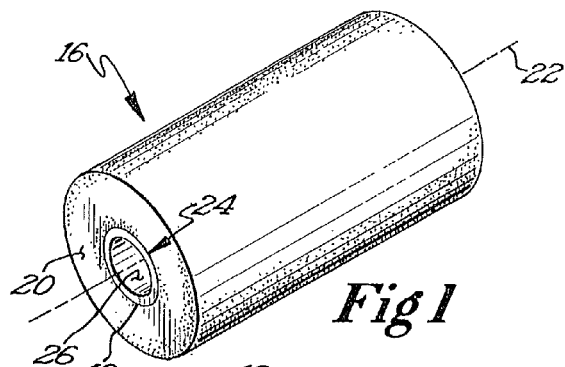
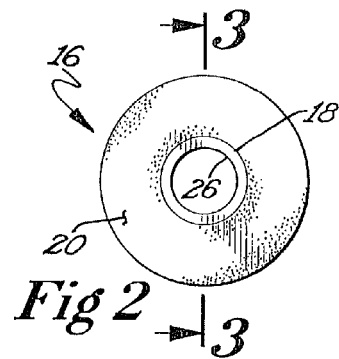
*Fig 1*  *Fig 2*
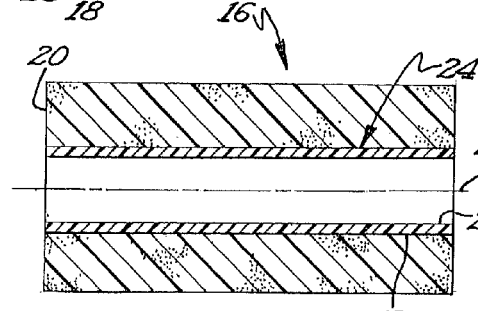
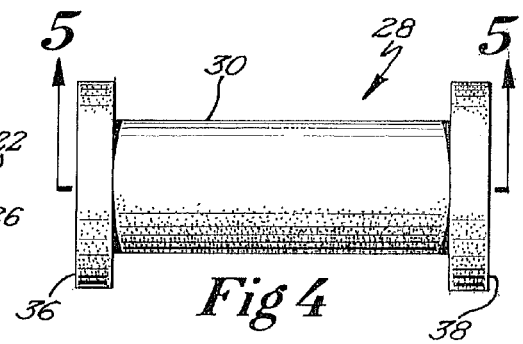
*Fig 3*  *Fig 4*
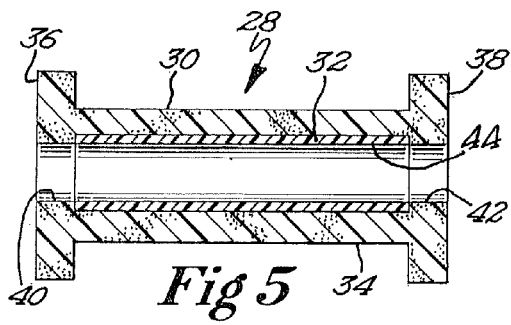
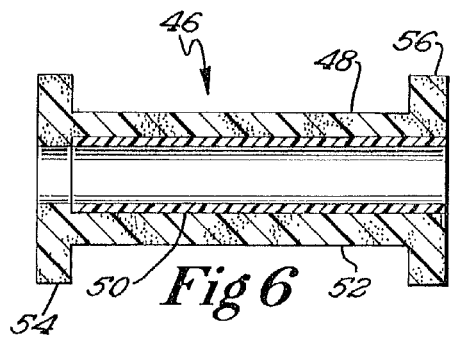
*Fig 5*  *Fig 6*
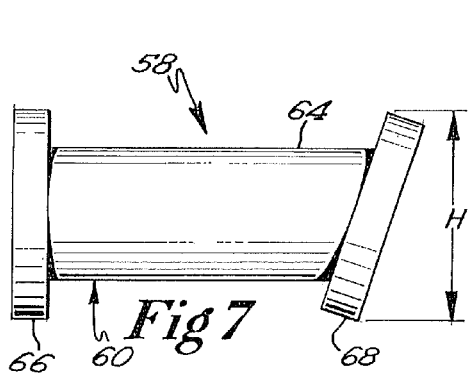
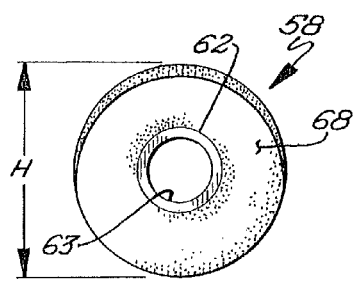
*Fig 7*  *Fig 8*

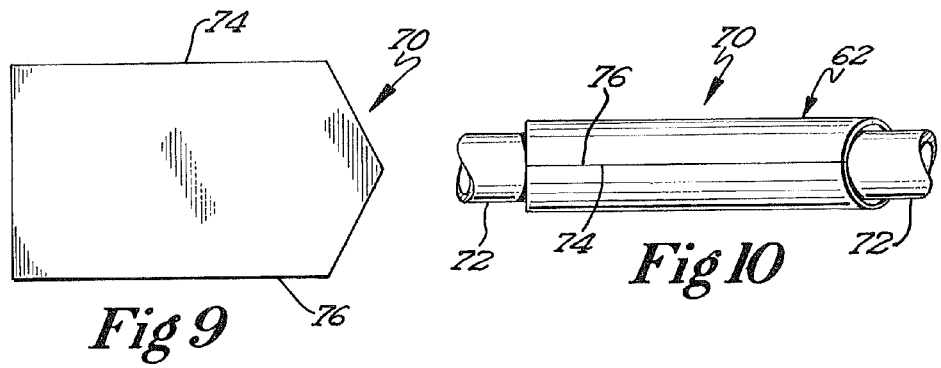
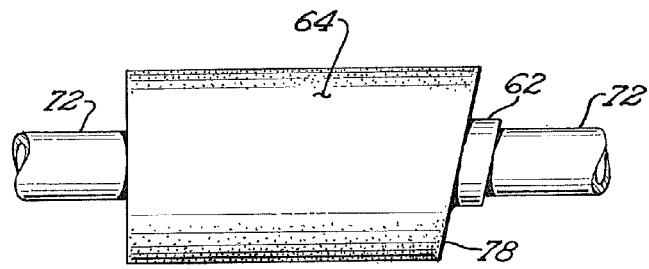
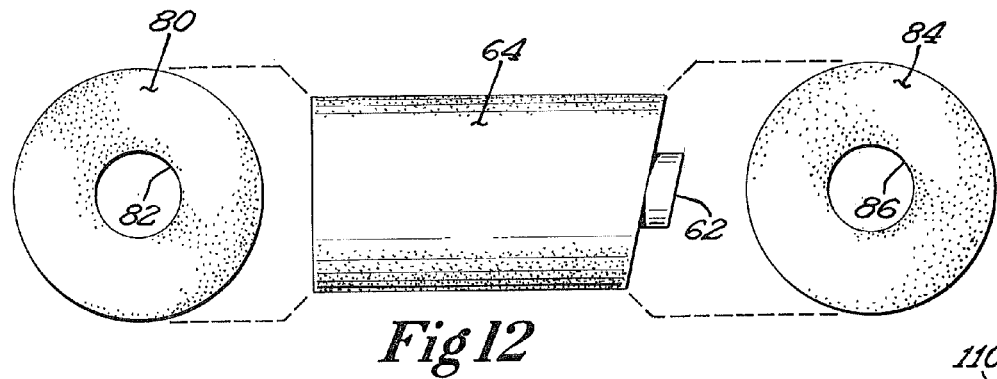
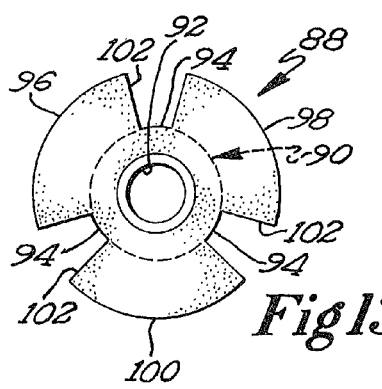
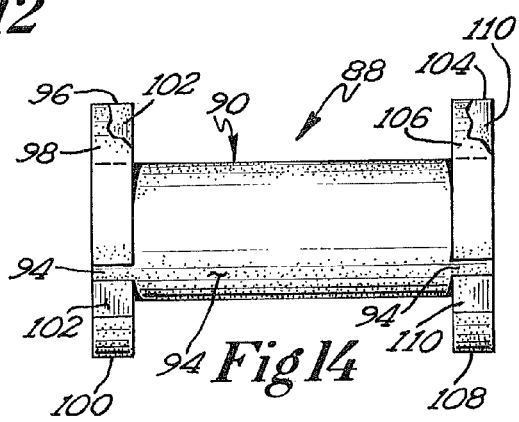

BIODEGRADABLE PROSTHESIS

This application claims the benefit of priority based on Provisional Application No. 61/219,447 entitled "Biodegradable Tympanic Membrane Prosthesis," filed Jun. 23, 2009.

BACKGROUND OF THE INVENTION

The present invention relates to body insertable prosthetic devices designed to maintain openings for ventilation, drainage of fluids and delivery of medications, and more particularly to prostheses designed to promote tissue healing while maintaining patency of a lumen surrounded by the healing tissue.

Otitis media, inflammation of the middle ear, is one of the most common childhood diseases. This condition frequently involves a build up of fluid in the middle ear, known as otitis media with effusion (OME), estimated to affect over two million individuals each year. The fluid accumulation applies pressure to the tympanic membrane (eardrum) that can be painful and can lead to hearing loss, interfere with speech and language development, and damage the tympanic membrane and other middle ear structures.

The most common surgical treatment of this condition, known as a myringotomy, involves forming an incision through the tympanic membrane, followed by insertion of a PE (pressure equalization) tube into the incision. As the tympanic membrane heals around the tube, a lumen through the tube remains patent to enable fluid drainage and ventilate the middle ear space. PE tubes are also placed to facilitate delivery of medications to the middle ear to treat such disorders as sudden hearing loss and Meniere's Disease.

In other sites, e.g. the paranasal sinuses, a similar tubular prosthesis structure with a lumen can be used to drain fluid from a sinus or to irrigate a sinus while providing a stent to prevent narrowing of the passage. Present sinus stents are non-biodegradable and require removal either in a second operative setting or in a clinic, with significant discomfort to the patients.

A variety of PE tubes have been developed over the years. Examples are seen in U.S. Pat. No. 4,468,218 (Armstrong), U.S. Pat. No. 5,053,040 (Goldsmith III), U.S. Pat. No. 7,097,661 (Perry), and in published international application, Publication No. WO 2008/036368 (Cottler). The tubes are formed from a variety of body compatible materials including polytetrafluoroethylene (PTFE) and other suitable fluoroplastics, silicone, gold, titanium, and their alloys. A typical tube includes an elongate shaft or tube designed to reside in the tympanic membrane incision, and opposite end flanges, each with a diameter larger than the shaft diameter. The flanges are adapted for location on opposite sides of the tympanic membrane to more positively secure the shaft in the incision. Alternative designs employ only one flange at the inner or distal end of the shaft for placement against the medial side of the tympanic membrane.

One problem with this type of ventilation tube is the lack of control over the length of time the tube remains in place. The tubes are subject to spontaneous extrusion from the tympanic membrane. Premature loss of the tube in this fashion results in the need for further surgery to replace the tube. The medial side flanges can be enlarged or otherwise configured to counteract the spontaneous extrusion tendency. This, however, increases the difficulty of initial insertion through the incision, and increases the difficulty of removing the tube after it is no longer needed. Thus, the lack of control can involve either a premature spontaneous extrusion or an undesirable tendency to remain in place beyond the time needed for treatment.

Another problem with the conventional ventilation tube is the risk of a persistent perforation of the tympanic membrane once the tube has extruded. Although this problem arises in just a small percentage of procedures, it underscores the need for promoting tissue healing and closure of the incision.

It has been proposed to eliminate the need for removal by forming the tube of a biodegradable material. U.S. Pat. No. 4,650,488 (Bays) discloses a prosthesis in which polymers of lactic acid, e.g. poly (DL-lactide), are used to form the entire ventilation tube, or at least the shaft plus the medial flange. The shaft is tapered, diminishing in diameter in the inward direction, so that once the shaft dissolves, the medial flange falls into the middle ear and the lateral flange falls outward into the external ear canal. Bays notes that degradation time can be varied through material selection, radiation, and size.

U.S. Pat. No. 7,163,557 (D'Eredita) discloses a biodegradable prosthesis formed of resorbable polyphosphazenes. Like Bays, D'Eredita mentions radiation as a means to increase the speed of degradation, and notes a preference for dissolving the central body or shaft before the flanges.

U.S. Pat. No. 6,379,323 (Patterson) is directed to a myringotomy tube formed of gelatin, more particularly as sold under the brand name GELFILM. Patterson advises that the gelatin shaft of the tube tends to loose its lumen patency and collapse upon itself if the internal diameter is not made large enough, specifically at least about 2.0 mm.

Although the biodegradable prostheses can eliminate the need for surgical removal of ventilation tubes, they encounter difficulties in simultaneously addressing essential and desirable prosthesis features which compete with one another. For example, in many applications it is necessary for the prosthesis to maintain its structural integrity in situ for several weeks or more, especially in terms of maintaining lumen patency for better fluid drainage and ventilation. This suggests the need for a relatively large size and relatively slow resorption or degradation rate. Conversely, the need to promote the healing of tissue and closure of the incision suggest the need for a smaller size and higher degradation rate. The hemostatic function of the prosthesis indicates the need for a porous, absorbent structure, while a smoother, less porous structure would provide more effective drainage of fluids from the middle ear.

In addition, the biodegradable prostheses disclosed to date do not adequately address the need to promote tissue healing and closure of the incision. The D'Eredita patent includes material critical of polylactides, contending that they involve the risk of growth of granulation tissues consequent upon their imperfect absorption by the tissues, and does not address the need for hemostatic properties.

Accordingly, the present invention has several aspects, each directed to one or more of the following objects:

to provide a tubular prosthesis resorbable in situ in a manner that more reliably maintains patency of a lumen through a tube, and promotes healing of surrounding tissue for closure of an incision or perforation through which the tube extends;

to provide a resorbable tympanic membrane prosthesis with hemostatic properties and porocity at least throughout its radially outward regions to enhance its function as a hemostatic device;

to provide a composite tubular prosthesis with a resorbable tubular inner layer with a smooth lumen wall for enhanced flow of fluids through the lumen, combined with a coaxial outer layer with a higher porocity and higher resorbtion rate; and to provide a structurally self-supporting body absorbable prosthesis that advantageously incorporates denatured gelatin sponge material to promote healing and closure of an opening in tissue through which the prosthesis extends.

SUMMARY OF THE INVENTION

To achieve these and other objects, there is provided a tympanic membrane prosthesis. The prosthesis includes a structurally self supporting body compatible and body absorbable device incorporating denatured gelatin sponge material. The device has proximal and distal ends, and a lumen open at both ends and running through the device. The device is adapted for insertion into an opening through a tympanic membrane for placement with the proximal and distal ends disposed on opposite sides of the tympanic membrane.

Several alternative approaches may be used to incorporate the gelatin sponge material. According to one approach, the material is incorporated as a unitary gelatin sponge, cut and rolled or otherwise formed into the desired tubular shape. In this approach, the sponge preferably constitutes an outer layer of a composite tube that further includes a coaxial inner layer that resorbs in situ at a slower rate than the sponge. More preferably, the inner layer is smoother and less porous than the gelatin sponge.

In other approaches the gelatin is fragmented, in powdered form or as small cut pieces of the sponge. The particles or fragments are dispersed throughout a solid, body absorbable, structurally self-supporting medium. As compared to a unitary gelatin sponge, the medium-supported dispersion is more rigid, yet retains hemostatic properties and promotes healing of adjacent surrounding tissue.

Another aspect of the present invention is a body compatible resorbable layered ventilation tube. The tube includes a tubular member disposed about a longitudinal axis, comprising a tubular first layer having a first resorption rate and defining a lumen running longitudinally through the tubular member, and a tubular second layer surrounding the first layer, substantially coaxial with the first layer, and having a second resorbtion rate greater than the first resorption rate.

Following insertion of the prosthesis into a tympanic membrane perforation or incision, the second or outer layer is resorbed at a faster rate than the first or inner layer. The result is a more rapid reduction of the prosthesis profile as viewed in a transverse plane. The tissue regrowth around the reduced size profile promotes an earlier closure of the perforation, following the complete resorbtion of the prosthesis. At the same time, the slower degradation rate of the inner layer operates to ensure lumen patency in spite of the diminishing prosthesis profile. The inner layer tends to retain its structural integrity, preserving the size of the lumen and smoothness of the lumen surface to more efficiently conduct fluids along the lumen.

In preferred versions of the prosthesis, the outer layer is substantially more porous and absorbent than the inner layer. The higher porosity and absorbtivity enable the outer layer to function as a hemostatic device immediately after prosthesis insertion. Surrounded by and in contact with tympanic membrane tissue after insertion into the incision, the outer layer absorbs the blood and promotes thrombosis.

In contrast, the less porous inner layer forms a smoother inside surface that defines the lumen. This results in lower friction and resistance to fluid flow, for a more efficient conduction of fluids through the prosthesis.

Relative degradation rates of the inner and outer layers can be influenced by their relative size, particularly as to relative radial thickness, and the materials selected. In any event, selective differences in degradation rate, porosity and absorbtivity provide a prosthesis with absorptive and hemostatic properties where most needed, long term structural integrity where most needed, and the capability of promoting tissue healing and growth leading to closure of the tympanic membrane perforation following complete resorbtion of the prosthesis.

Another aspect of the present invention is a body insertable prosthesis. The prosthesis includes a body compatible device adapted for placement in a body adjacent tissue. The device comprises a resorbable first constituent forming a solid and structurally self supporting medium, and a resorbable second constituent forming a fragmentary dispersion in suspension throughout the medium. The second constituent is porous, has hemostatic properties, and tends to produce an inflammatory reaction in adjacent tissue as the second constituent breaks down in situ.

The fragmentary distribution can take the form of cut fragments of the second constituent. Alternatively, the second constituent can be provided in particulate or powdered form. The second constituent can consist essentially of a denatured gelatin sponge material, provided as cut fragments of the sponge, or a particulate or powdered form of the sponge.

In either event, the fragmented constituent is combined with a liquid to form a substantially homogenous mixture with a paste-like consistency. The paste is malleable, and readily formed into a tubular shape or other desired shape by injecting the paste into a mold. The paste solidifies as it dries, forming a solid-self supporting medium in which the second constituent is suspended.

A highly preferred liquid is a prescription ear drop incorporating an antibiotic and a steroid.

IN THE DRAWINGS

For a further understanding of the above and other features and advantages, reference is made to the following detailed description and to the drawings, in which:

FIG. 1 is a perspective view of a tubular prosthesis formed in accordance with the present invention;

FIG. 2 is an end elevation of the prosthesis;

FIG. 3 is a side sectional view of the prosthesis taken along the line 3-3 in FIG. 2;

FIG. 4 is a side elevational view of an alternative embodiment prosthesis;

FIG. 5 is a sectional view of the prosthesis taken along the line 5-5 in FIG. 4;

FIG. 6 is a sectional view similar to that of FIGS. 3 and 5, showing another alternative embodiment prosthesis;

FIG. 7 is a side elevation of a further alternative embodiment prosthesis;

FIG. 8 is an end elevation showing the prosthesis of FIG. 7;

FIGS. 9-12 illustrate fabrication of the prosthesis shown in FIG. 7;

FIG. 13 is an end elevation of another alternative embodiment prosthesis;

FIG. 14 is a side elevation showing the prosthesis of FIG. 13;

DETAILED DESCRIPTION OF THE PREFERRED EMBODIMENTS

Figure 15:
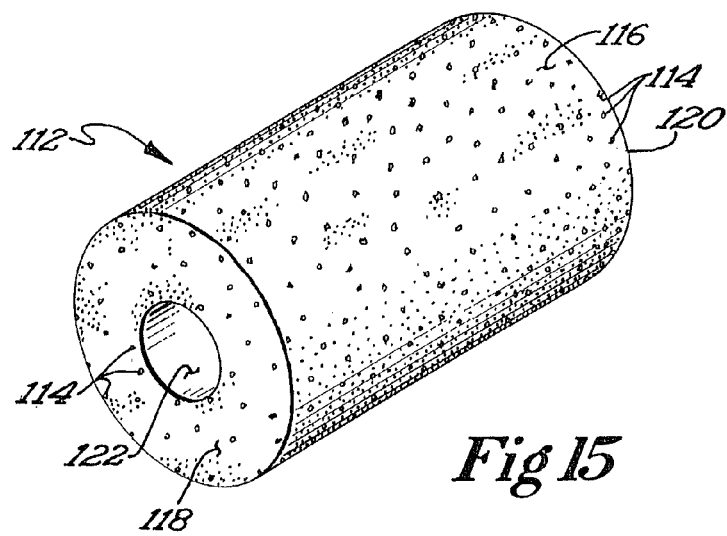
FIG. 15 is a perspective view of a further alternative embodiment tubular prosthesis.

Turning now to the drawings, FIGS. 1-3 illustrate a tubular prosthesis 16 constructed in accordance with the present invention. The prosthesis includes an elongate tubular inner layer 18 and a tubular outer layer 20, both disposed concentrically about a longitudinal tube axis 22. The outer layer surrounds the inner layer and has an inside surface which is contiguous with an outer surface of the inner layer. As best seen in FIG. 2, layers 18 and 20 have annular profiles in transverse planes, i.e. planes perpendicular to the tube axis. Layers 18 and 20 have respective radial thickness dimensions, each preferably uniform over the circumference and axial length of its associated layer.

Prosthesis 16 is composed of biodegradable materials. More particularly, inner layer 18 is composed of an inner layer material that tends to degrade at a first degradation rate when situated in tissue and exposed to body fluids. Outer layer 20 is composed of an outer layer material tending to degrade at a second degradation rate when situated in body tissue and exposed to body fluids. The second degradation rate is substantially higher than the first degradation rate.

In addition, while the inner layer material has a relatively low capacity for absorbing liquids and tends to form smooth outer surfaces, the outer layer material is highly absorptive and highly porous.

A highly preferred first layer material is an absorbable gelatin film available from Pharmacia & Upjohn Company of Kalamazoo, Mich. under the brand name GELFILM. When dry, the film has the appearance and texture of a cellophane film having the same or similar thickness. The dry film also is sufficiently rigid to exhibit a self supporting structural integrity in the manner of a hard plastic. When moistened, the film becomes pliable, and can be cut to a desired size and formed into a desired shape.

Several characteristics of the gelatin film render it particularly well suited for the inner layer material. The capability of complete absorption after implantation eliminates the need for surgical removal. At the same time, its rate of absorption or degradation in situ is relatively low, taking from about one to six months after implantation, depending primarily on the size (particularly the thickness) of inner layer 18 and the implantation site. As a result, the inner layer can be kept relatively thin to facilitate implantation, yet retain sufficient structural integrity to maintain the patency of a lumen 24 after implant for ventilation and fluid drainage.

The smooth texture of the gelatin film is useful in providing a smooth inside surface 26 of the inner layer, providing a more efficient flow of fluids through lumen 24. Due to the lower absorption rate, the inside surface retains its smooth character for a longer time, again for more effective fluid passage through the lumen, whether to drain fluids from the middle ear or to conduct fluid treatment agents to the middle ear.

The gelatin film is body compatible and suitable for placement in the region of the middle ear, where it has been used as a barrier to prevent tissue adhesions and to promote perforation closure.

A highly preferred outer layer material is a surgical sponge material made from denatured gelatin, available from Pharmacia & Upjohn Company under the brand name GELFOAM. The gelatin sponge is porous, highly absorptive, and flexible. The gelatin sponge also is structurally self supporting, tending to recover its nominal shape when no longer subject to compression or another force causing elastic deformation.

The gelatin sponge is particularly well suited as the outer layer material in that it is absorbed completely over time, eliminating the need for surgical removal. Its rate of absorption or degradation is considerably higher than that of the gelatin film of inner layer 18.

Over a time period immediately following implantation, the high absorptivity and porosity of the gelatin sponge enable outer layer 20 to function as a hemostatic device. The outer layer receives and absorbs body fluids, particularly blood, from the newly formed tympanic membrane incision. The flexible outer layer tends to conform to the shape of the incision for maximum surface contact. The surface contact and mechanical matrix provided by the sponge are believed to be the primary factors that facilitate clotting. In addition, as the gelatin sponge dissolves, it promotes tissue healing and closure of an incision, wound or other perforation in the tympanic membrane.

The gelatin sponge is body compatible and suitable for placement in the region of the middle ear. The gelatin sponge is frequently used in a variety of procedures to pack the middle ear space.

Over the long term following implantation, a reduction in the prosthesis profile, particularly as taken in transverse planes, enables and facilitates epithelial growth and tissue regeneration about and into the outer layer. This gradually diminishes the size of the perforation through the tympanic membrane, to the point that membrane tissue surrounds and contacts inner layer 18 after the outer layer has been nearly or completely absorbed.

To further facilitate and promote healing in the region of the incision, outer layer 20 can be impregnated with treatment agents, e.g. growth factors such as basic fibroblast growth factor (bFGF), anti-inflammatory agents, and anti-bacteriological agents. This can be accomplished by providing treatment agents in liquid form for absorption into outer layer 20 before implantation. For example, treatment agents may be incorporated into a sterile saline solution in which prosthesis 16 is immersed. This step is best performed well in advance of implantation to ensure that prosthesis 16 is sufficiently dry to recover its self supporting, substantially rigid character.

Frequently there is a need to counteract a premature, spontaneous extrusion of the prosthesis from the tympanic membrane or other implantation site. To this end, an alternative version prosthesis 28 is shown in FIGS. 4 and 5. Prosthesis 28 includes a tubular member 30 similar to prosthesis 16 composed of inner and outer layers 32 and 34. In addition, a proximal (lateral) flange 36 is secured to a proximal end of tubular member 30 and a distal (medial) flange 38 is fixed to a distal end of the tubular member. Flanges 36 and 38 are disk-shaped, with circular profiles in planes perpendicular to a tube axis of prosthesis 28. Central openings 40 and 42 through flanges 36 and 38 ensure that a lumen 44 extends along the complete length of the prosthesis.

As before, the inner layer material is smoother, less porous, and has a substantially slower rate of absorption or degradation as compared the outer layer material of tubular member 30. Flanges 36 and 38 preferably are composed of a more absorptive, porous, biodegradable material with a higher degradation rate. The flanges and outer layer 34 can be composed of the same material.

FIG. 6 illustrates a further alternative prosthesis 46 including a tubular member 48 composed of an inner layer 50, and outer layer 52 surrounding the inner layer, a proximal flange 54 and a distal flange 56. Prosthesis 46 is similar to prosthesis 28. However, in prosthesis 46, the inner tubular layer extends to the distal end of the prosthesis, surrounded by distal flange 56 as well as the outer tubular member. As before, the inner tubular member degrades in situ at a relatively slow rate while the remainder of the prosthesis degrades at a more rapid rate. Accordingly, with the prosthesis deployed in the tympanic membrane, inner tubular layer 50, as compared to its counterpart tubular inner layer 32, extends further beyond the tympanic membrane. This effectively counteracts any tendency for epithelial growth to cover the inner tubular member distal end and prematurely close or reduce the lumen.

As a further alternative embodiment, either of prostheses 28 and 46 can be fabricated with a single flange, namely the distal or medial flange. The prosthesis no longer is securely anchored at both ends, but continues to effectively counteract spontaneous extrusion outwardly away from the middle ear.

FIGS. 7 and 8 illustrate a further alternative prosthesis 58, preferred from the standpoint of providing easier insertion as well as secure placement following implantation. The prosthesis includes a tubular member 60 having an inner tubular layer 62 defining a lumen 63 and an outer tubular layer 64 concentric on the tube axis. A distal end of the tubular member is oblique, inclined at an angle of about thirty degrees from a transverse plane. A proximal end flange 66 is bonded to the tubular structure and as before is aligned with its major plane perpendicular to the tube axis. Distal end flange 68 is fixed to the distal end of the tubular structure as before. In contrast to earlier versions, the major plane of flange 68 is inclined to match the inclination of the distal edge of the tubular member. The outer diameter of flange 68 is larger than the outer diameter of proximal flange 66 at least in directions parallel to the plane of FIG. 7, such that profiles of the two flanges as projected onto transverse planes have approximately the same height H as indicated in FIG. 7.

As in earlier versions of the prosthesis, distal flange 68 cooperates with proximal flange 66 to secure the prosthesis within the tympanic membrane incision following implantation. In addition, the inclined distal end flange eases deployment of the prosthesis. More particularly, when prosthesis 58 is aligned to position the leading or distal edge of flange 68 adjacent the tympanic membrane incision with its length dimension substantially aligned with the length of the incision, the flange is capable of functioning as a funnel or wedge to guide the prosthesis into the insertion.

Consistent with previous versions of the prosthesis, prosthesis 58 is completely biodegradable. Inner tubular layer 62 is formed of the more stable and less porous material, while outer tubular layer 64 and flanges 66 and 68 are formed of the more hemostatic, porous, and more rapidly degradable material.

Fabrication of prosthesis 58 begins with providing a sheet of biodegradable material, e.g. the gelatin film described above, in the desired size and shape. The sheet material is available in a thickness of 0.075 mm, which is suitable for this purpose. As shown in FIG. 9, the end of a flat sheet 70 slated to become the distal end of tubular layer 62 is inclined at the desired angle, in this case thirty degrees. Before the sheet material is cut, it is moistened, for example by immersion in a saline solution, to render it more pliable and amenable to cutting.

While sheet 70 remains moist, it is shaped around a cylindrical form 72 to align opposite side edges 74 and 76 as seen in FIG. 10. As sheet 70 dries, it retains its cylindrical shape with side edges 74 and 76 confronting one another.

Next, outer tubular layer 64, formed of the gelatin sponge and cut to the desired size and shape, is placed onto the form to surround inner tubular layer 62, as shown in FIG. 11. The proximal ends of the tubular layers are aligned. A distal end 78 of outer tubular layer 64 is recessed relative to a distal end of inner tubular layer 62

In an alternative approach, sheet 70 and a similarly sized sheet of the gelatin sponge material are joined to form a two-layered generally planar composite film. Typically the gelatin sponge layer is thicker, and slightly shorter to provide the previously mentioned distal end recess. Then, the composite film is moistened and shaped into the desired cylinder.

As shown in FIG. 12, a proximal end disk 80 is formed of the gelatin sponge, with a central opening 82 sized to correspond to an inside diameter of inner tubular layer 62. A gelatin sponge distal disk 84 also is formed, with a relatively larger diameter and a central opening 86 sized to accommodate the portion of inner tubular layer 62 that projects beyond the outer tubular layer. Disks 80 and 84 are mounted to the opposite ends of the tubular structure to complete the prosthesis. The disks are retained on the tubular structure by a friction fit, or by an adhesive.

The prosthesis at this point may be immersed in a liquid solution incorporating growth factors and other treatment agents for application of the agents to surrounding tissue following implantation. As noted above, this step should be completed before the prosthesis is implanted, to allow sufficient drying time to restore the self supporting character to the prosthesis. In an alternative approach, a growth factor or other treatment agent can be delivered to the gelatin foam outer layer after implantation.

In one preferred version of the prosthesis, lumen 63 through tubular member 60 has a length of 1 mm (or about 1.25 mm including its extension through disks 80 and 84) and a diameter of 1.50 mm. Proximal flange 66 and distal flange 68 have diameters of about 3.0 mm. Alternatively, distal flange 68 can have a slightly larger diameter, e.g. 3.3 mm, for a profile in the transverse direction comparable to that of flange 66.

FIGS. 13 and 14 illustrate another alternative prosthesis 88 including a tubular member 90 with inner and outer tubular layers 92 and 94. In lieu of opposite end flanges, proximal end tabs 96, 98, and 100 extend radially outwardly from the proximal end of outer layer 94. Like the outer layer, tabs 96-100 are formed of the gelatin sponge material. Three relatively narrow regions 102, disposed between adjacent proximal end tabs, are adapted to be held by forceps or another gripping tool. When a gripping tool is used to support prosthesis 88 at one of regions 102 during insertion, the risk of damage to the prosthesis from the gripping tool is minimized.

Three distal end tabs 104, 106, and 108 extend radially outwardly from the distal end of outer layer 94. Narrow regions 110, disposed between adjacent distal end tabs, function in the same manner as regions 102 to provide locations at which prosthesis 88 can be held by a gripping tool while avoiding or minimizing the risk of prosthesis damage.

Another feature of prosthesis 88 is that distal tabs 104-108, as compared to a continuous annular flange such as flange 38, 56, or 68, more readily yield to facilitate passage of the prosthesis distal end through a tympanic membrane incision during deployment.

FIG. 15 illustrates a further alternative embodiment prosthesis 112. In a departure from the two-tiered structures previously described, prosthesis 112 has a substantially homogeneous tubular body including fragments or particles 114 of denatured gelatin sponge material dispersed throughout a solid, self supporting and resorbable medium 116. The body has a proximal end 118 and a distal end 120. A lumen 122 runs lengthwise through the body, open at the proximal and distal ends. The medium is continuous, in the sense that it occupies the interstices between adjacent particles or fragments of the gelatin sponge. The fragments are distributed substantially uniformly throughout the tubular body.

The gelatin sponge fragments are shown schematically as black dots to illustrate their presence. In actual practice, the density of the particles or fragments is considerably higher than that suggested in the figure. Also, the fragments or particles are not visibly distinct from medium 116 in the finished product.

Figure 16:
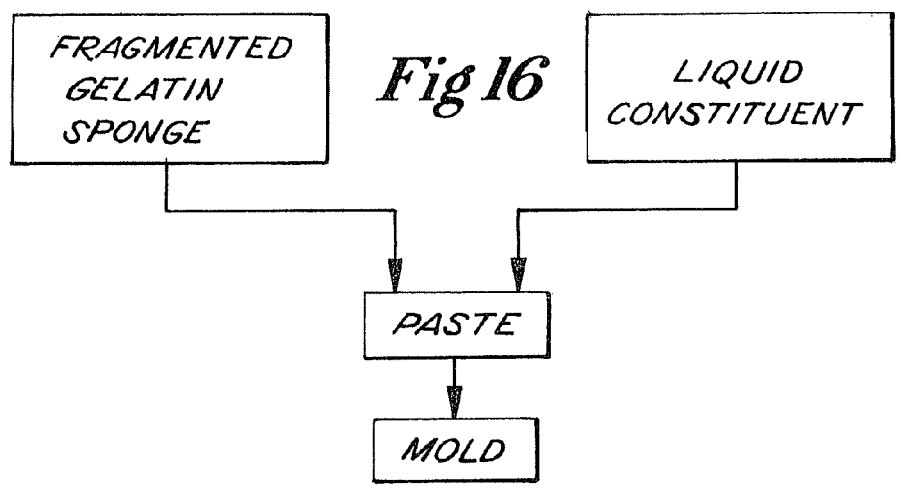
FIG. 16 is a diagrammatic view illustrating fabrication of the prosthesis of FIG. 15.

The fabrication of prosthesis 112, illustrated in FIG. 16, begins with providing fragmented denatured gelatin sponge material, for example the material noted above as available under the brand name GELFOAM. The fragmented material can be provided by cutting a thin (typically less than 0.01 inches thick) sheet of the gelatin sponge into small fragments. Alternatively, a sterile powder of the gelatin sponge can provide particulate fragments.

The fragmented gelatin sponge material is combined with a liquid constituent to form a viscous, malleable doughy paste. This is accomplished by gradually adding the liquid constituent to the fragmented gelatin sponge while kneading the mixture to provide a more uniform mixture. The liquid constituent is added until the desired paste-like consistency is achieved.

At this stage the paste is loaded into a mold, e.g. by injection using a syringe. To form prosthesis 112, the mold defines a cylindrical chamber and includes an elongate cylindrical fixture centered in the chamber to form lumen 122.

Once loaded into the mold, the paste is allowed to dry at ambient temperatures. As it dries, the mixture solidifies or sets into a solid, self-supporting structure. After the structure is removed from the mold, slight trimming or other material removal may be required to finish the prosthesis.

In an alternative approach, a paste having the desired consistency is shaped by hand about an elongate cylindrical fixture, e.g. a pin. After the paste has dried to form a solid body, the body is carved or shaved, e.g. with a precision rotary tool sold under brand name DREMEL to provide the finished cylindrical shape. The fixture is removed from the body to provide the lumen.

It has been found that the paste mixture has a tendency to shrink as it sets, particularly when the gelatin sponge material is provided as cut fragments. Accordingly, where size is critical and cut fragments of the gelatin sponge are employed, the carving or shaving approach may be preferred. Alternatively, the shrinking tendency also can be counteracted with an oversized mold. In any event, either approach can be employed to achieve a desired prosthesis size and shape. For example, the prosthesis can be shaped to provide proximal and distal end flanges, and the distal end flange may be oblique.

The following examples are presented to enhance an understanding of the process and the resulting prosthesis.

Example 1

A malleable paste is formed by combining gelatin powder and an antibiotic and steroid liquid otic preparation (eardrop). A preferred eardrop, available under the brand name CIPRODEX, incorporates ciprofloxacin hydrochloride as the antibacterial agent and dexamethasone as an anti-inflammatory corticosteroid, in purified water. Sodium hydroxide or hydrochloric acid may be added to adjust the pH.

Approximately 5 ml of the eardrop is added gradually in approximately 0.05 ml drops to 1 gram of GELFOAM absorbable gelatin powder. The mixture is kneaded as the eardrop is added, to provide a paste of the desired consistency and uniformity. The paste is shaped around a pin having a diameter corresponding to the desired lumen diameter, formed approximately into the desired tubular shape, and allowed to dry. The dried body is carved into the desired tubular shape, and the pin is removed to provide the lumen.

Example 2

The process is essentially similar to that of Example 1, except that 3-4 ml of a sterile saline solution are added to the powdered gelatin sponge in lieu of the eardrop.

Example 3

A prosthesis structure is formed in essentially the same manner as Example 1, with the exception that a larger pin is employed to foam a lumen with a larger diameter. After the body has solidified, a sheet of GELFILM gelatin film (thickness of 0.075 mm) is moistened, then cut to a rectangular shape and size corresponding to the desired lumen diameter. The moistened rectangular piece is bent or rolled into a tubular shape and inserted lengthwise into the lumen of the previously formed body. The gelatin film retains the tubular shape as it sets.

In the preceding examples, cut fragments of the gelatin sponge can be used in lieu of the gelatin sponge powder, and molds can be used to reduce or eliminate the need to carve or shave material from the hardened body.

Prosthesis 112, homogenous rather than layered, nonetheless combines the following favorable qualities: (1) structural integrity that facilitates use of a gripping instrument to convey the prosthesis to the intended treatment site and to insert the prosthesis into the incision or perforation, with negligible risk of crumbling, crushing, of breakage; (2) a radially outward region that breaks down in situ to promote closure of an incision or other opening through the tympanic membrane; and (3) patency of the lumen to conduct fluids, whether for drainage or to admit fluid treatment agents. The gelatin sponge material, although fragmented, retains the tendency to produce an inflammatory reaction in tissue adjacent and surrounding the prosthesis, promoting healing and eliminating the need to "freshen" the edges of an eardrum perforation before inserting the prosthesis. Using the antibiotic and steroid eardrop as the liquid constituent, as in Example 1, releases an antibacterial agent and an anti-inflammatory agent as the medium and fragmented gelatin sponge are resorbed, to fight bacterial infection and mitigate the inflammatory reaction to the resorbing gelatin sponge material.

In an alternative approach, a prosthesis similar to prosthesis 112 has a substantially homogeneous tubular body formed by rolling or bending a sheet of denatured gelatin sponge into the desired tubular shape. More generally, any of the previously described embodiments can be constructed with just the single layer of the gelatin sponge.

Figure 17:
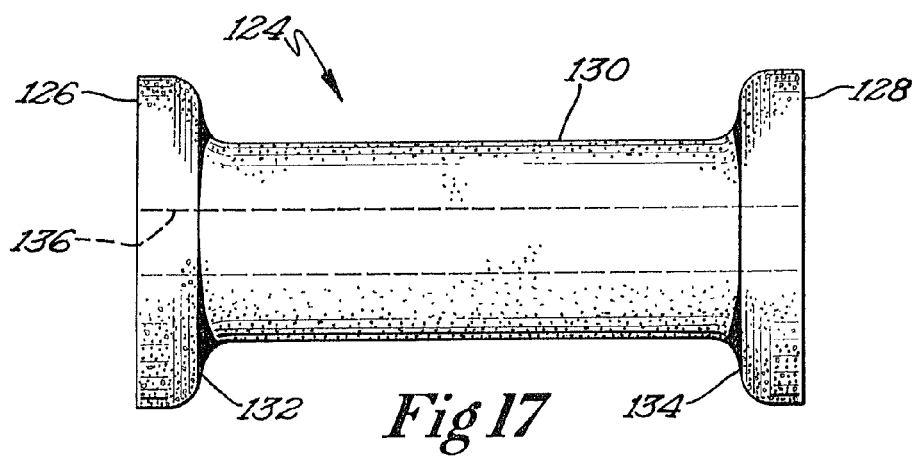
FIG. 17 is a side elevation of another alternative embodiment prosthesis.

FIG. 17 illustrates another alternative embodiment prosthesis 124. Prosthesis 124 has an elongate body which, like the body of prosthesis 112, is substantially homogenous with fragments or particles of denatured gelatin sponge material dispersed throughout a solid, self supporting and resorbable medium. As before, the medium is continuous, and the fragments are distributed substantially uniformly.

Prosthesis 124 is symmetrical about a longitudinal axis, generally having an hourglass profile in longitudinal planes containing the axis. The body includes enlarged proximal and distal end regions 126 and 128 and a narrower central region 130. A transition region 132 between central region 130 and proximal end region 126, and a similar transition region 134 between the central region and distal end region 128, provide for gradual increases in diameter from the central region to the end regions. In terms of the profile, the gradual transition can constitute a curve as shown, or a more linear incline.

Proximal and distal end regions 126 and 128 provide lateral and medial enlargements positionable on opposite sides of the tympanic membrane, to more positively locate central region 130 in the perforation and to counteract spontaneous extrusion of the prosthesis. In other words, the enlarged end regions perform the functions of flanges such as flanges 36 and 38 in prosthesis 28 (FIG. 4). As compared to prostheses with end flanges, prosthesis 124 affords the advantages of relative ease in its manufacture, and increased structural strength and stability through the more gradual changes in prosthesis diameter.

In procedures where there is no need for a lumen to admit fluid treatment agents or provide drainage, prosthesis 124 takes the form of a solid, homogenous plug insertable through an ear drum perforation to locate the proximal and distal end regions on opposite sides of the ear drum. Resorption of the prosthesis promotes healing of tissue around the central region, and eventual closure of the perforation.

Alternatively, prosthesis 124 can be formed with a longitudinal central lumen as indicated in broken lines at 136 to conduct fluids past the ear drum. Whether the prosthesis is formed as a tube or a plug, the preferred liquid constituent used in fabrication is an antibiotic and steroid liquid otic preparation as in Example 1 above.

Further alternative prostheses involve forming a denatured gelatin sponge into a plug or a tubular prosthesis with the profile of prosthesis 124. As compared to prosthesis 124, a prosthesis consisting of the gelatin sponge is more flexible, with a distal end region that more readily yields elastically to facilitate insertion through a tympanic membrane incision. Conversely, procedures requiring more structural stability or sustained lumen patency favor the gelatin sponge suspension.

Prostheses formed in accordance with the present invention can be employed in a wide variety of procedures relating to the ear drum and sinuses. For example, a prosthesis may be used before transtympanic steroid or gentamycin injection. A prosthesis may be used during tympanomastoidectomy surgery to maintain equalization of middle ear pressure while the tympanic membrane graft heals. The prosthesis may be used in the course of hyperbaric oxygen treatment and for inoperative ABR when fluid is present in the middle ear.

In another application, the prosthesis is inserted into a small perforation in the tympanic membrane (either acute or chronic) to promote closure. In these applications, a growth factor can be imbedded into the gelatin sponge for application to the tissue to promote healing.

Prostheses according to the present invention may be employed for children who need pressure equalization tubes for periods shorter than six to eighteen months, and for fluid drainage from the middle ear in adults with symptomatic acute or chronic serous otitis media.

Finally, although the forgoing description is directed primarily to prostheses intended for placement in the ear, the principles can be employed to fabricate prostheses intended for other placements, e.g. in the sinuses or nasal passages.

What is claimed is:

1. A tympanic membrane prosthesis, including:
   a structurally self supporting body compatible and body absorbable device incorporating denatured gelatin sponge material, the device having proximal and distal ends and a lumen open at said ends and running through the device, wherein the device is adapted for insertion into an opening through a tympanic membrane for placement with the proximal and distal ends disposed on opposite sides of the tympanic membrane, and further adapted to maintain patency of the lumen following said insertion and placement,
   the absorbable device incorporating denatured gelatin sponge material dispersed in a self-supporting medium.

2. The prosthesis of claim 1 wherein: the device comprises the self-supporting medium, and the denatured gelatin sponge material forms a fragmentary dispersion in suspension throughout the medium.

3. The prosthesis of claim 2 wherein: the fragmentary dispersion of the gelatin sponge material comprises a gelatin sponge powder.

4. The prosthesis of claim 1 wherein: the device comprises an elongate tubular member disposed about a longitudinal axis.

5. The prosthesis of claim 4 wherein: the device further comprises a medial flange disposed proximate the distal end and having a flange diameter greater than an outer diameter of the tubular member.

6. The prosthesis of claim 5 wherein: a major plane of the medial flange is oblique relative to the longitudinal axis.

7. The prosthesis of claim 4 wherein: the device further comprises a plurality of tabs extending radially away from the tubular member proximate the distal end.

8. The prosthesis of claim 1 wherein: the device comprises a tubular outer layer incorporating the gelatin sponge material and having a first resorption rate, and an inner layer surrounded by the outer layer and having a second resorption rate lower than the first resorption rate.

9. The prosthesis of claim 8 wherein: the inner layer consists essentially of a gelatin film.

10. The prosthesis of claim 1 wherein: the device further incorporates a treatment agent selected from the group of treatment agents consisting of: antibiotics, and steroids.

11. A tympanic membrane prosthesis, including:
    a structurally self supporting body compatible and body absorbable device incorporating denatured gelatin sponge material, the device having proximal and distal ends and a lumen open at said ends and running through the device, wherein the device is adapted for insertion into an opening through a tympanic membrane for placement with the proximal and distal ends disposed on opposite sides of the tympanic membrane, and further adapted to maintain patency of the lumen following said insertion and placement,
    the absorbable device consisting of denatured gelatin sponge material dispersed in a self-supporting medium.

12. The prosthesis of claim 11 wherein: the device comprises the self-supporting medium, and the denatured gelatin sponge material forms a fragmentary dispersion in suspension throughout the medium.

13. The prosthesis of claim 12 wherein: the fragmentary dispersion of the gelatin sponge material comprises a gelatin sponge powder.

14. The prosthesis of claim 11 wherein: the device comprises an elongate tubular member disposed about a longitudinal axis.

15. The prosthesis of claim 14 wherein: the device further comprises a medial flange disposed proximate the distal end and having a flange diameter greater than an outer diameter of the tubular member.

16. The prosthesis of claim 15 wherein: a major plane of the medial flange is oblique relative to the longitudinal axis.

17. The prosthesis of claim 14 wherein: the device further comprises a plurality of tabs extending radially away from the tubular member proximate the distal end.

18. The prosthesis of claim 11 wherein: the device further incorporates a treatment agent selected from the group of treatment agents consisting of: antibiotics, and steroids.

* * * * *